United States Patent
Skalicky

(10) Patent No.: US 12,290,315 B2
(45) Date of Patent: May 6, 2025

(54) METHOD AND/OR SYSTEM FOR TESTING VISUAL FUNCTION

(71) Applicant: Eyeonic Pty Limited, Victoria (AU)

(72) Inventor: Simon Skalicky, Victoria (AU)

(73) Assignee: Eyeonic Pty Limited, Victoria (AU)

( * ) Notice: Subject to any disclaimer, the term of this patent is extended or adjusted under 35 U.S.C. 154(b) by 488 days.

(21) Appl. No.: 17/760,824

(22) PCT Filed: Sep. 16, 2020

(86) PCT No.: PCT/AU2020/050982
§ 371 (c)(1),
(2) Date: Mar. 16, 2022

(87) PCT Pub. No.: WO2021/051162
PCT Pub. Date: Mar. 25, 2021

(65) Prior Publication Data
US 2022/0338728 A1    Oct. 27, 2022

(30) Foreign Application Priority Data

Sep. 16, 2019  (AU) ................................ 2019903438

(51) Int. Cl.
*A61B 3/024* (2006.01)
*A61B 3/00* (2006.01)
(Continued)

(52) U.S. Cl.
CPC ............ *A61B 3/024* (2013.01); *A61B 3/0041* (2013.01); *A61B 3/032* (2013.01); *G06N 20/00* (2019.01)

(58) Field of Classification Search
CPC ....... A61B 3/024; A61B 3/0041; A61B 3/032; A61B 5/0022; A61B 5/4842;
(Continued)

(56) References Cited

U.S. PATENT DOCUMENTS

| 6,227,668 B1 | 5/2001 | McKinnon |
| 6,592,222 B2 | 7/2003 | Massengill |

(Continued)

FOREIGN PATENT DOCUMENTS

| AU | 701075 | 11/1995 |
| CA | 2373684 A1 | 11/2000 |

(Continued)

OTHER PUBLICATIONS

International Preliminary Report on Patentability dated Mar. 15, 2022, for PCT/AU2020/050982, filed Sep. 16, 2020.
(Continued)

*Primary Examiner* — Mohammed A Hasan
(74) *Attorney, Agent, or Firm* — Paul D. Bianco; Fleit Intellectual Property Law

(57) ABSTRACT

A method for performing an eye test includes the steps of: receiving a request from a user to perform the eye test; acquiring predetermined user identification data from the user; presenting or providing at least one test image to the user, the at least one test image including at least one test target contained therein; instructing the user to identify at least one of the at least one test target(s) contained within the at least one test image; acquiring response data associated with the user's attempt(s) to identify the at least one test target(s) contained within the at least one test image; aggregating and/or analysing the acquired user identification data and/or the response data utilising a test algorithm which determines result data; and, presenting or providing the result data to the user.

17 Claims, 10 Drawing Sheets

(51) Int. Cl.
 *A61B 3/032* (2006.01)
 *G06N 20/00* (2019.01)
(58) Field of Classification Search
 CPC ............ A61B 2560/0223; A61B 3/022; A61B 3/0033; A61B 5/7264; A61B 5/7275; A61B 5/7475; G06N 20/00; G16H 40/63; G16H 50/20; G09G 2320/0693; G01J 1/4204
 USPC .......................................................... 351/224
 See application file for complete search history.

(56) References Cited

U.S. PATENT DOCUMENTS

| | | | |
|---|---|---|---|
| 8,657,446 | B2 | 2/2014 | Weleber |
| 8,967,809 | B2 | 3/2015 | Kirschen |
| 9,572,484 | B2 | 2/2017 | Palanker |
| 2003/0158497 | A1* | 8/2003 | Graham ................ A61B 5/378 600/558 |
| 2008/0024724 | A1 | 1/2008 | Todd |
| 2016/0239625 | A1 | 8/2016 | Berry |
| 2016/0270656 | A1* | 9/2016 | Samec ................ A61B 3/1015 |
| 2017/0273553 | A1* | 9/2017 | Greivenkamp, Jr. ........................ A61B 3/0041 |
| 2017/0360293 | A1 | 12/2017 | Novik |
| 2018/0008142 | A1 | 1/2018 | Garoon |
| 2018/0249151 | A1 | 8/2018 | Freeman |
| 2019/0150727 | A1 | 5/2019 | Blaha |
| 2019/0200858 | A1* | 7/2019 | Yam ........................ A61B 3/032 |
| 2021/0007597 | A1* | 1/2021 | Ooi ........................ G02B 27/017 |
| 2022/0192482 | A1* | 6/2022 | Liu ........................ A61B 3/024 |

FOREIGN PATENT DOCUMENTS

| | | | |
|---|---|---|---|
| WO | 2001/072212 | A1 | 10/2001 |
| WO | 2010/129663 | A1 | 11/2010 |
| WO | 2015/063598 | A1 | 5/2015 |
| WO | 2016/179370 | A1 | 11/2016 |

OTHER PUBLICATIONS

International Search Report dated Nov. 23, 2020, for PCT/AU2020/050982, filed Sep. 16, 2020.
Written Opinion for PCT/AU2020/050982, filed Sep. 16, 2020.
Chris A. Johnson, "Screening for Glaucomatous Visual Field Loss With Frequency-Doubling Perimetry", Investigative Ophthalmology & Visual Science, Feb. 1997, vol. 38, No. 2, 13 pages.
Johnson et al, "Frequency Doubling Technology Perimetry Using a 24-2 Stimulus Presentation Pattern", Optometry and Vision Science, vol. 76, No. 8, Aug. 1999, pp. 571-581.
Vingrys et al, "A New Look at Threshold Estimation Algorithms for Automated Static Perimetry", Optometry and Vision Science, 1999, vol. 76, No. 8, pp. 588-595.
Vinesh Sukumar et al, "Study on Threshold Patterns with Varying Illumination Using 1.3m Imaging System", Intelligent Information Management, 6 p. 2010.
"WCAG definition of relative luminance" from WCAP WG, Jul. 31, 2013-Oct. 22, 2020, 2 pages.
Skalicky et al, "Activity Limitation in Glaucoma: Objective Assessment by the Cambridge Glaucoma Visual Function Test", Investigative Ophthalmology and Visual Science, Nov. 2016, vol. 57, No. 14, 58 pages.
Yu Xiang George Kong et al, "A Comparison of Perimetric Results from a Tablet Perimeter and Humphrey Field Analyzer in Glaucoma Patients", Transl Vis Sci Technol., Nov. 2016, 2 pages.
Jones et al., "Portable Perimetry Using Eye-Tracking on a Tablet Computer—A Feasibility Assessment", TVST, vol. 8, No. 1, Article 17, 2019, 11 pages.
European Search Report dated Dec. 19, 2022, for European Patent No. 20864512.7.

* cited by examiner

METHOD AND/OR SYSTEM FOR TESTING VISUAL FUNCTION

CROSS-REFERENCE

This Application claims the benefit of Australian Provisional Patent Application No.: 2019903438, filed on 16 Sep. 2019, and International Patent Application No.: PCT/AU2020/050982, filed on 16 Sep. 2020, the entire contents of which are incorporated herein by reference thereto.

FIELD OF THE INVENTION

The present invention relates generally to visual function testing.

The present invention has been developed primarily for testing for vision changes of glaucoma by a method and/or system and will be described hereinafter with reference to this application. However, it will be appreciated that the invention is not limited to this particular field of use. A skilled person will appreciate other relevant visual function tests, variations or alternatives thereof, applicable for use with the method and/or system of the present invention. Accordingly, the present invention as hereinafter described should not be construed as limited to any one or more of the specific examples provided herein.

BACKGROUND OF THE INVENTION

Any discussion of documents, devices, acts or knowledge in this specification is included to explain the context of the invention. It should not be taken as an admission that any of the material forms a part of the prior art base or the common general knowledge in the relevant art in Australia, or elsewhere, on or before the priority date of the disclosure herein.

Vision loss can commonly occur due to clouding of the eye lens as in the case of cataracts, damage of the optic nerve as in the case of glaucoma, or due to degeneration of the retina, as commonly seen in age-related macular degeneration. Glaucoma and macular degeneration can cause irreversible loss of vision and blindness.

Glaucoma is the second leading cause of blindness and the leading cause of irreversible blindness worldwide. There are estimated to be approximately 300,000 individuals afflicted by glaucoma in Australia, with approximately 50% of these instances being undiagnosed. This is largely because not everyone is willing or has the means to attend a screening with an optometrist or ophthalmologist.

Individuals afflicted with severe glaucoma have difficulty performing visually demanding tasks. This difficulty impacts daily life activities such as driving, walking, and reading amongst others. The abilities to see in dimly lit circumstance, peripheral objects, and to judge distances are also affected, which can result in accidents.

The development of glaucoma is gradual and is often undetected in its early stages. Symptoms may not be apparent to the afflicted individual until irreversible loss of vision has already occurred. Early detection of vison changes from glaucoma can therefore be a crucial step to treating glaucoma.

Features of glaucoma can normally be detected during a visit to an optometrist for a regular eyeglasses or contact lenses prescription check-up. During a check-up an optometrist may conduct an eye pressure check, a visualisation of the optic nerve, and a peripheral vision check which may be used to diagnose the onset of various eye problems or illnesses, including glaucoma. However, many individuals do not wear glasses or contact lenses, others may choose not to wear them or may not be aware that they need them and they may rarely or never visit an optometrist.

Subjective methods of testing visual function are critical to evaluating a person's visual function. They may be complemented by objective tests of vision which have a less important role in evaluating a degree of visual compromise. Subjective methods of testing visual function include central visual functions such as measuring contrast sensitivity and visual acuity, for which the targets are discernible targets, requiring distinction from the form of other similar targets. Visual field testing (otherwise known as "perimetry") is another subjective method of testing visual functions. This occurs by the user being asked to gaze at a central fixation target, while other targets are shown in the eye's periphery. Such targets are tested at a locus chosen randomly from a set of predetermined loci, at different levels of brightness. Perimetry targets involve detection (i.e. was the target seen or not) as opposed to discernment (i.e. what type of target was it), wherein the user is asked to voluntarily respond (e.g. by way of clicking a button or the likes) when they consciously detect a target in their peripheral field. These tests are generally required to be performed under qualified supervision in a clinic. The results obtained in these tests may be limited as these tests do not reflect real-world visual function because of their clinical settings. For example, in a real-world scenario individuals can adjust their head and eyes to compensate for loss of peripheral vision, and external brightness will likely differ from that within a clinic and varies throughout the day in the real world.

Questionnaires (also known as patient reported outcomes or PRO's) can be used to subjectively evaluate an individual's abilities to perform visually related tasks. However, aspects such as psychological factors, personality and recall bias may influence an individual's responses and could create an obstacle to detecting glaucoma.

The subjective, clinical or artificial nature of the above-mentioned and similar tests can be somewhat overcome by objective testing methods of visual simulation scenarios, some of which resemble real-world scenarios.

Objective tests performed by optometrists and ophthalmologists, including retina scanning, using tonometry to check intraocular pressure, checking for optic nerve damage using an ophthalmoscope, or checking pupillary light responses, require the use of special imaging equipment and the involvement of specialists or technicians to ensure the test is performed correctly. The limitations of these tests include their duration, complexity, high costs and the portability of the large and bulky equipment used. In addition, these tests have a different clinical purpose then subjective tests of vision—while they may reflect physiological parameters of the eye's health, they are not a measure of what the patient reports they see. In addition, many individuals may find these types of tests, as well as convention visual field tests, uncomfortable.

The above-mentioned eye tests are all conducted manually and usually operator dependent. The require precisely manufactured and manually calibrated equipment. This approach necessarily prolongs the duration of the tests and has inherent potential for human error to affect diagnosis and early detection of glaucoma, and also increases barriers to access to healthcare including cost and necessitating attendance at a clinic that has such specialised equipment.

It would therefore be desirable to provide a method and/or system which overcomes or alleviates one or more of the aforesaid problems associated with known visual function tests for detecting glaucoma, or which at least provides a useful alternative.

It would also be desirable to provide an easy, subjective method and/or system for detecting glaucoma that is reflective of real-world visual function, and which can be taken by an individual on a computing device in an individual's home or at another convenient location.

SUMMARY OF THE INVENTION

Accordingly, in one aspect, the present invention provides a method for performing a subjective visual field test to evaluate a user's monocular peripheral vision at specific loci, without the need for dedicated professional equipment or qualified professional supervision, but instead via the use of at least one computing device configured to access at least one dedicated visual field test server, accessible via a communications network, the method including the steps of: receiving a request from a user to perform the visual field test via the at least one computing device, acquiring predetermined user identification data from the user and/or the at least one computing device in response to predetermined instructions from the at least one dedicated visual field test server; presenting or providing for a required number of iterations at least one test image to the user via at least one display of the at least one computing device, the at least one test image including at least one test target contained therein that is shown at at least one predetermined location in the user's peripheral visual field, whilst the user is gazing at a focus point; instructing the user to identify if they have detected the presence of at least one of the at least one test target(s) contained within the at least one test image; acquiring response data associated with the user's attempts to identify the at least one test target(s) contained within the at least one test image; aggregating and/or analysing, via the at least one dedicated visual field test server, the acquired user identification data and/or the response data utilising a test algorithm which determines overall result data; and, presenting or providing the visual field test overall result data to the user via the at least one computing device; wherein the predetermined user identification data acquired from the user and/or the at least one computing device includes data which is used to configure the test parameters for performance of the visual field test; wherein the at least one predetermined location of the least one test target shown in the user's peripheral visual field may vary with each required iteration of the presentation or provision of the at least one test image; and, wherein the at least one test target(s) is circular and waveform in appearance and the apparent waveform traverses the at least one test target(s).

Accordingly, in a further aspect, the present invention provides a visual field test graphic including: the graphic being adapted for displaying at least one luminance-configurable colour at a predetermined frequency.

Preferably, the graphic has at least two graphic segments for alternatingly displaying in at least one graphic segment the at least one luminance-configurable colour at a predetermined frequency.

Preferably, the graphic is curviplanar in appearance. It is also preferred that the graphic is waveform in appearance and the apparent waveform traverses the graphic. Preferably, the waveform is sinusoidal.

Preferably, one or more of the peaks or troughs of the waveform defines the at least one graphic segment.

Preferably, the graphic has a circular perimeter and the waveform traverses the centre and the perimeter of the graphic.

Preferably, the at least one luminance-configurable colour includes one or more background colour of the graphic.

Preferably, the at least one luminance-configurable colour is displayed by being faded in and/or out including to and/or from the at least one luminance-configurable colour.

Preferably, the at least one luminance-configurable colour is presented at a predetermined frequency for a predetermined period in one or more intervals. It is also preferred that the predetermined frequency is approximately 10 Hz to 110 Hz and the predetermined period is about 0.55 seconds.

Preferably, the presentation of the at least one luminance-configurable colour creates a varied contrast during the predetermined period. It is also preferred that the varied contrast is increasing contrast.

Accordingly, in yet a further aspect, the present invention provides a method for determining relative luminance for a visual field test graphic, the method including the steps of: assigning each Red/Green/Blue ("RGB") colour component an integer value ("CRGB") between 0 and 255; converting each component's CRGB integer value to equate with a respective component decimal value ("CD"), which is calculated as CRGB/255; if the CD of a component >0.03928, applying the formula CL=(CD+0.055/1.055)2.4 to determine the linear value of the component ("CL"); if the CD of a component <0.03928, applying the formula CL=(CD/12.92 to determine the linear value of the component ("CL"); and, adding the CL of each component to obtain a relative luminance ("RL").

Accordingly, in still yet a further aspect, the present invention provides a method for determining the relative decibel ("rdB") of the RL of two colours RL1 and RL2 by applying the formula rdB=−2 log(RL1−RL2)/(RL1+RL2).

Preferably, the rdB of the RL of three or more colours is determined by applying a mathematical formula adapted to determine the rdB of three or more colours.

Preferably, the luminance of the at least one luminance-configurable colour is a RL determined according to the method for determining relative luminance for a visual field test graphic as described above.

Preferably, the rdB of at least two luminance-configurable colours are determined according to the method for determining the relative decibel as described above.

Preferably, the rdB of at least three luminance-configurable colours are determined according to the method wherein the rdB of the RL of three or more colours is determined by applying a mathematical formula adapted to determine the rdB of three or more colours. It is also preferred that the rdB is between the range of about 6 to about 36 dB.

Accordingly, in still yet a further aspect, the present invention provides a method for calibrating a display for a visual field test, the method including the steps of: measuring test-local light conditions to acquire corresponding data; processing the test-local light conditions data to determine calibration values; and, calibrating the display according to the one or more determined/predetermined values.

Preferably, the test-local light conditions are measured via a sensor associated with the display.

Preferably, the test-local light conditions are measured and corresponding data acquired and processed via a mobile device and the mobile device provides information for calibrating the display.

Preferably, the test-local light conditions are measured via a mobile device and the acquired data is communicated via a network to a processing unit associated with the display and the display is calibrated by the processing unit.

Preferably, the method for calibrating a display includes a step of displaying on the display the visual field test graphic so that the display is calibrated when the test-local light conditions including at least the test-local light condition of the visual field test graphic is measurable to within predetermined light quality parameters suitable for a visual field test.

Preferably, the step of instructing the user to identify at least one of the at least one test target(s) contained within the at least one test image occurs before, with or after the step of presenting the at least one test image to the user.

Preferably, the step of instructing the user to identify at least one of the at least one test target(s) contained within the at least one test image, includes prompting the user to perform the visual field test monocularly.

Preferably, the step of acquiring response data associated with the user's attempt(s) to identify the at least one test target(s) contained within the at least one test image includes acquiring response data of the time taken by the user to identify at least one of the at least one test target(s).

Preferably, the at least one test image, and the at least one test target contained therein, is sourced and/or generated from/by: predetermined test images and/or test targets; external data sources; and/or, by the test algorithm.

Preferably, the step of presenting or providing at least one test image to the user includes a predetermined duration for receipt of a response(s).

Preferably, the step of utilising the test algorithm which determines the result data includes generating a map of eye locus performance based on the acquired user identification data and/or the response data.

Preferably, the at least one test image(s) is/are animated images.

Preferably, the opacity and/or tone of the at least one test target(s) is/are predetermined and/or adjustable.

Preferably, the difficulty of the visual field test is predetermined and/or adjustable.

Preferably, the at least one test image(s) is/are divided into loci. In a practical preferred embodiment, the at least one test image(s) is/are divided into up to 80 loci by gridlines that are visible or invisible to the user. Preferably, the loci comprise at least one test locus and at least one non-test locus. Again, in a practical preferred embodiment, the up to 80 loci comprise 52 test loci.

Preferably, the at least one non-test locus comprises one of at least two tonal values.

Preferably, the loci are arranged in a geometric pattern.

Preferably, at least one locus is a test target and defines at least one test locus.

Preferably, the at least one test target includes the test graphic.

Preferably, the at least one test target includes the test graphic wherein the luminance of the at least one luminance-configurable colour is a RL determined including the method for determining relative luminance for a visual field test graphic as described above.

Preferably, the at least one test target includes the test graphic wherein the rdB of at least two luminance-configurable colours have been determined including the method for determining the relative decibel ("rdB") of the RL of two colours RL1 and RL2 by applying the formula $rdB=-2 \log(RL1-RL2)/(RL1+RL2)$, and/or wherein the rdB of at least three luminance-configurable colours has been determined including the method wherein the rdB of the RL of three or more colours is determined by applying a mathematical formula adapted to determine the rdB of three or more colours, and/or, wherein the rdB is between the range of about 6 to about 36 dB.

Preferably, the test target includes at least one tonal value assignable corresponding to at least one difficulty value.

Preferably, the at least one test locus comprises at least one tonal or other visual value assignable to a corresponding at least one difficulty level.

Preferably, the at least one test target comprises at least one luminance-configurable colour assignable to a corresponding at least one difficulty level.

Preferably, the at least one test target comprises at least one rdB assignable to a corresponding at least one difficulty level.

Preferably, a display associated with the visual field test is calibrated according to the method described above.

Preferably, the at least one test image(s) includes the focus point positioned within the at least one test image(s). It is also preferred that the focus point is a moving optical element.

Preferably, an incorrect attempt(s) to identify the at least one test target(s) and/or the at least one test locus contained within the at least one test image(s) generates a false positive response data value.

Preferably, the step of presenting or providing at least one test image to the user includes presenting or providing at least one test image and at least one test target of lower or higher difficulty than a respective predetermined test difficulty.

Preferably, the step of aggregating and/or analysing the acquired user identification data and/or the response data, utilises a test algorithm to optimise the performance and/or accuracy of the visual field test.

Preferably, the test algorithm further includes artificial intelligence and/or machine learning and/or deep learning to optimise the performance and/or accuracy of the visual field test.

Preferably, the artificial intelligence and/or machine learning and/or deep learning is adapted to predetermine content and/or parameters of the visual field test, including the content and/or parameters of any one or more of the following: the at least one test image(s); the at least one test target(s); the at least one test graphic(s); the at least one test locus; the duration for receipt of response(s); the gridlines that are visible or invisible to the user; the opacity of the at least one test target(s); visual field test difficulty; the focus point; and the focus point location, based on any user identification data and/or the response data to optimise the performance and accuracy of the visual field test.

Preferably, the method further includes a blind spot determination test. It is also preferred that the blind spot determination test is used to determine user fixation loss from the focus point.

Preferably, user fixation loss is determined by presenting a graphic at the location of the blind spot so that if fixation loss occurs the graphic becomes visible to the user.

Preferably, user fixation loss is used to calibrate loci parameters including loci number and loci geometry.

Preferably, the blind spot determination test is used to determine optimum user distance from the display and the precise distribution of test loci on the display.

Accordingly, in still yet a further aspect, the present invention provides non-transitory computer readable medium storing a set of instructions that, when executed by a machine, causes the machine to execute a method for performing a visual field test, the method including the steps of: receiving a request from a user to perform the visual field test; acquiring predetermined user identification data from the user; presenting or providing at least one test image to the user, the at least one test image including at least one test target contained therein; instructing the user to identify at least one of the at least one test target(s) contained within the at least one test image; acquiring response data associated with the user's attempt(s) to identify the at least one test target(s) contained within the at least one test image; aggregating and/or analysing the acquired user identification data and/or the response data utilising a test algorithm which determines result data; and, presenting or providing the result data to the user.

Accordingly, in still yet a further aspect, the present invention provides a system for performing a visual field test including: one or more modules or applications for receiving a request from a user to perform the visual field test; one or more modules or applications for acquiring predetermined user identification data from the user; one or more modules of applications for presenting or providing at least one test image to the user, the at least one test image including at least one test target contained therein; one or more modules or applications for instructing the user to identify at least one of the at least one test target(s) contained within the at least one test image; one or more modules or applications for acquiring response data associated with the user's attempt(s) to identify the at least one test target(s) contained within the at least one test image; one or more modules or applications for aggregating and/or analysing the acquired user identification data and/or the response data utilising a test algorithm which determines result data; and, one or more modules or applications for presenting or providing the result data to the user.

Accordingly, in still yet a further aspect, the present invention provides a non-transitory computer readable medium storing a set of instructions that, when executed by a machine, causes the machine to execute a method for calibrating a display for a visual field test, the method including the steps of: measuring test-local light conditions to acquire corresponding data; processing the test-local light conditions data to determine calibration values; and, calibrating the display according to the one or more determined or predetermined values.

Accordingly, in still yet a further aspect, the present invention provides non-transitory computer readable medium storing a set of instructions that, when executed by a machine, causes the machine to execute a method for calibrating a display for a visual field test, the method including the steps of: measuring test-local light conditions to acquire corresponding data; processing the test-local light conditions data to determine calibration values; calibrating the display for the visual field test according to one or more predetermined values, wherein at least one of the one or more predetermined values is a RL of at least one colour determined by the steps including: assigning each RGB colour component an integer value ("CRGB") between 0 and 255; converting each component's CRGB integer value to equate with a respective component decimal value ("CD"), which is calculated as CRGB/255; if the CD of a component >0.03928, applying the formula CL=(CD+ 0.055/1.055)2.4 to determine the linear value of the component ("CL"); if the CD of a component <0.03928, applying the formula CL=(CD/12.92 to determine the linear value of the component ("CL"); and, adding the CL of each component to obtain a relative luminance ("RL"); determining the RL for a first colour ("RL1") and a second colour ("RL2").

Preferably, the method is adapted to determine the relative decibel ("rdB") of at least one colour further including the step of: determining the relative decibel ("rdB") of RL1 and RL2 by applying the formula rdB=−2 log(RL1−RL2)/(RL1+ RL2).

Accordingly, in still yet a further aspect, the present invention provides a system for calibrating a display for a visual field test, the system including: a display for calibrating; a test graphic displayable on the display; one or more modules/devices for data acquisition of test-local light conditions data; one or more data processing modules/devices for processing test-local light conditions data; one or more display calibration modules/devices for using acquired test-local light conditions data to calibrate the display or providing instructions for manually calibrating the display; and a communication system for communicating between said display and any one or more modules.

Preferably, the one or more modules for data acquisition, and/or one or more data processing modules, and/or one or more display calibration modules is a mobile device.

These and other essential or preferred features of the present invention will be apparent from the description that now follows.

BRIEF DESCRIPTION OF THE DRAWINGS

In order that the invention may be more clearly understood and put into practical effect there shall now be described in detail preferred visual field test methods and/or systems made in accordance preferred embodiments of the present invention. The ensuing description is given by way of non-limitative examples only and is with reference of the accompanying drawings, wherein.

Figure 1:
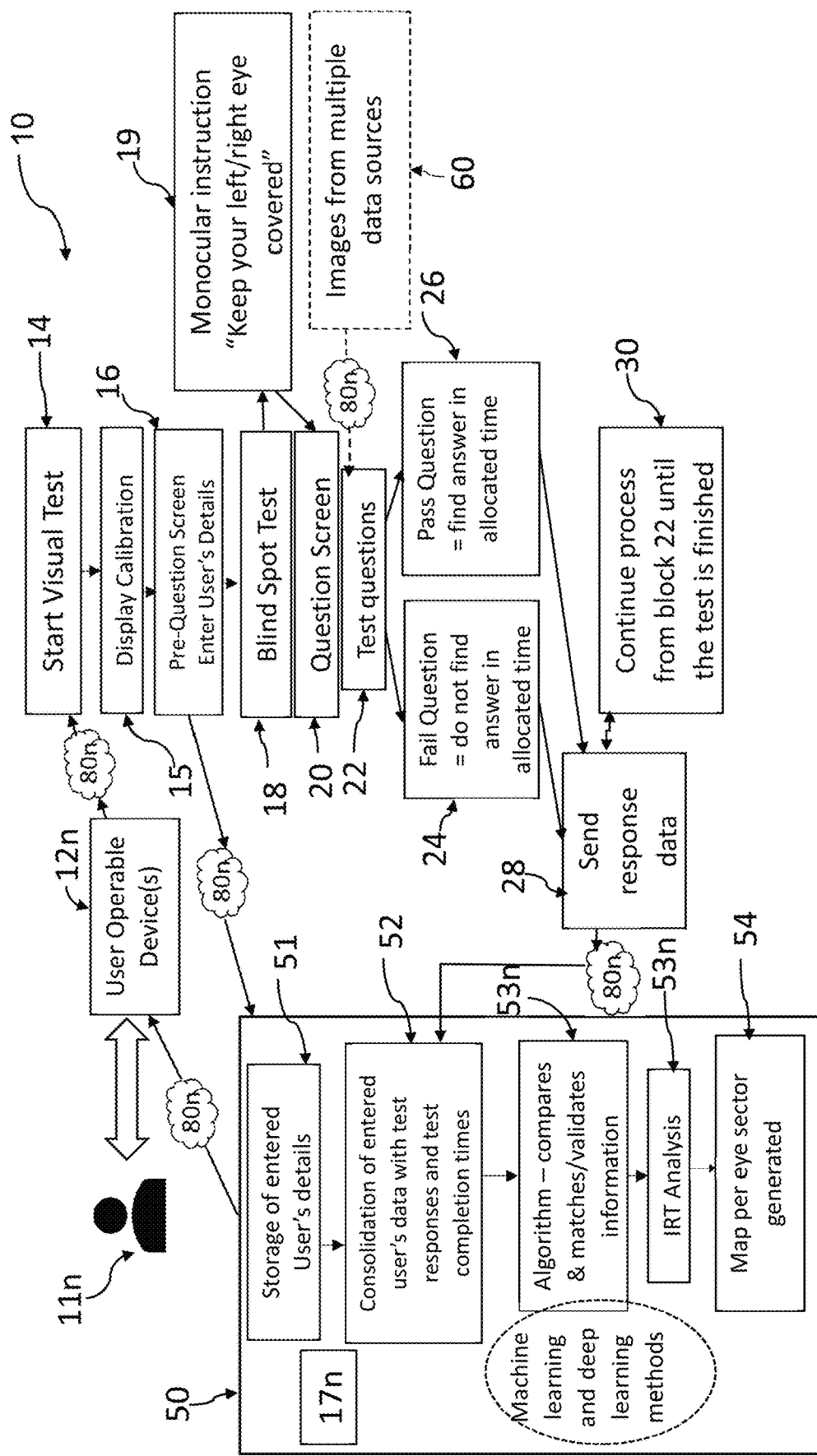
FIG. 1 is a block diagram of a preferred method and/or system for testing for visual function of a user, made in accordance with a preferred embodiment of the present invention.
Figure 2:
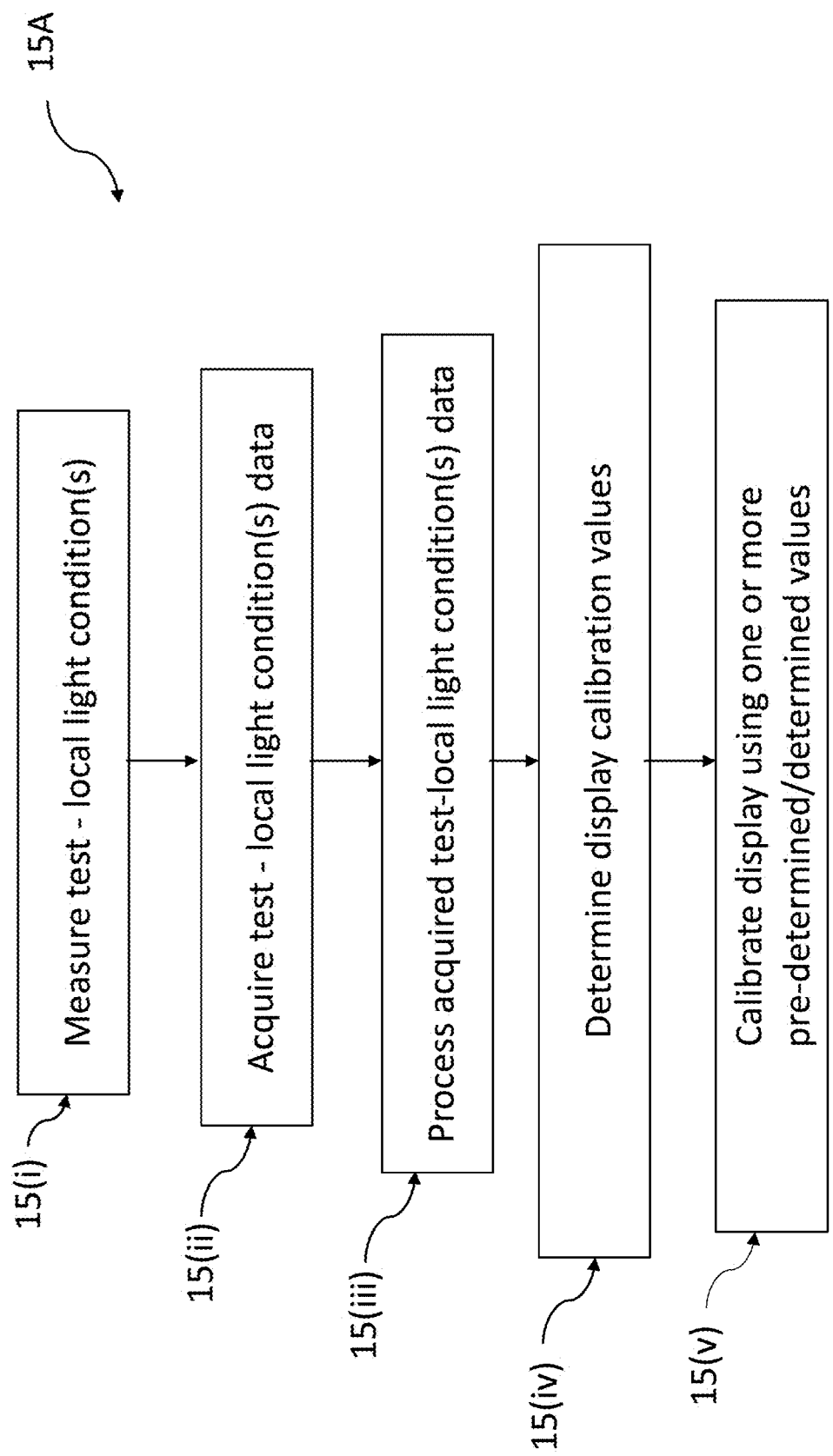
FIG. 2 is a flow diagram which illustrates a preferred method for calibrating a display for a visual field test, made in accordance with a preferred embodiment of the present invention and being suitable for use with the preferred method and/or system for testing for visual function shown in FIG. 1.
Figure 4:
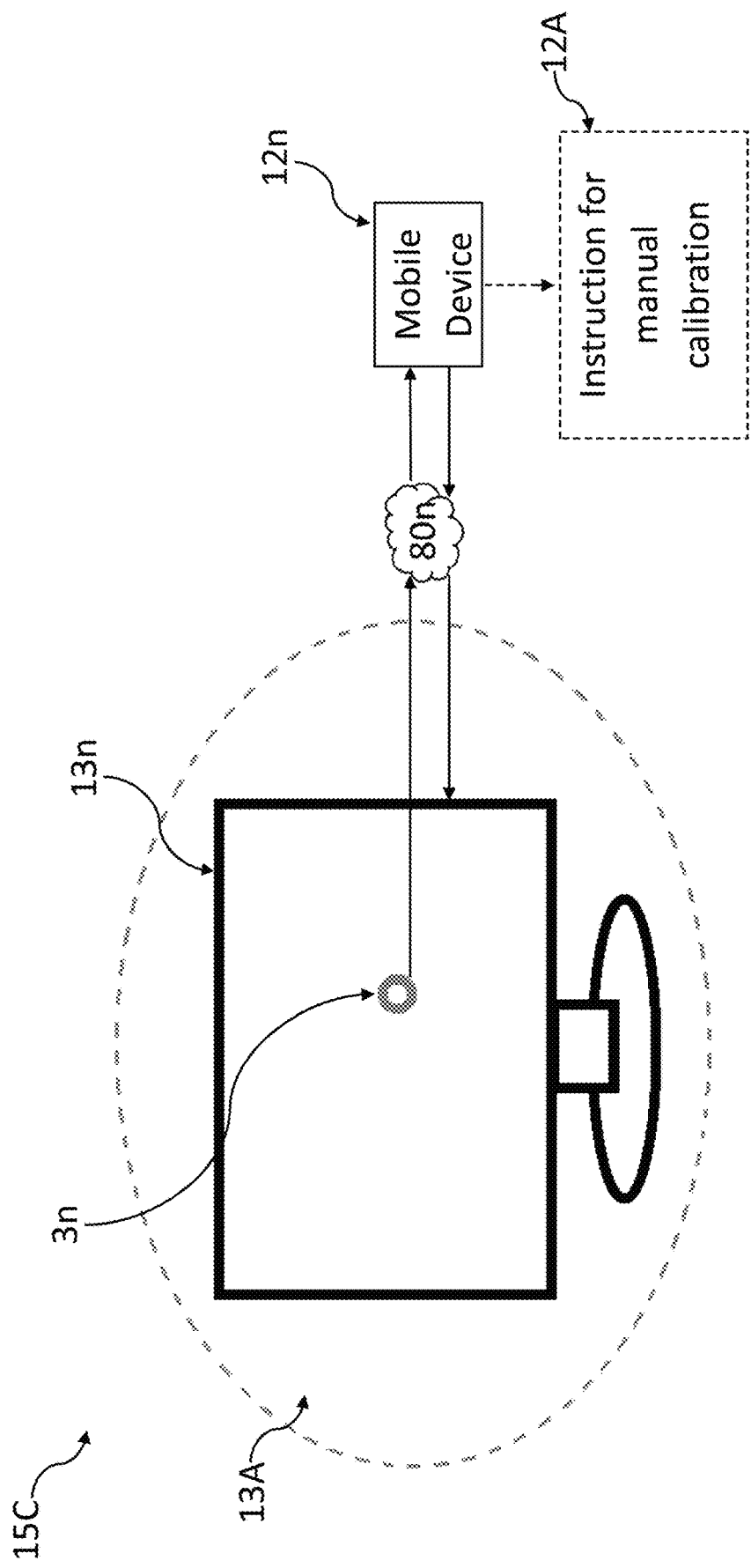
FIG. 4 is a block diagram which illustrates a preferred alternative system for calibrating a display for a visual field test including a visual field test graphic presented on a display associated with a mobile device, made in accordance with a preferred embodiment of the present invention and being suitable for use with the preferred method and/or system for testing for visual function shown in FIG. 1 and/or the method for calibrating a display for a visual field test shown in FIG. 2.
Figure 6:
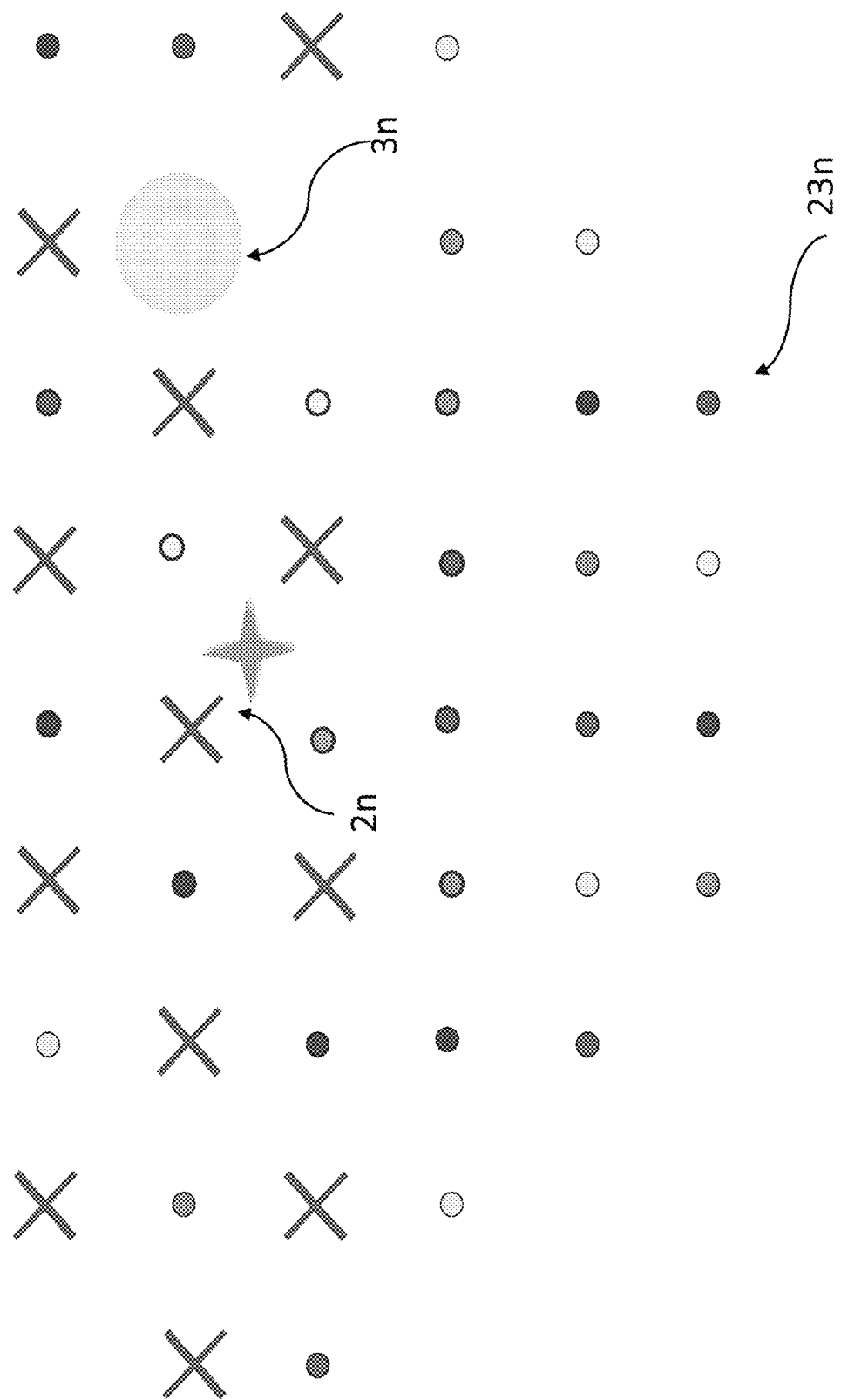
Figure 7:
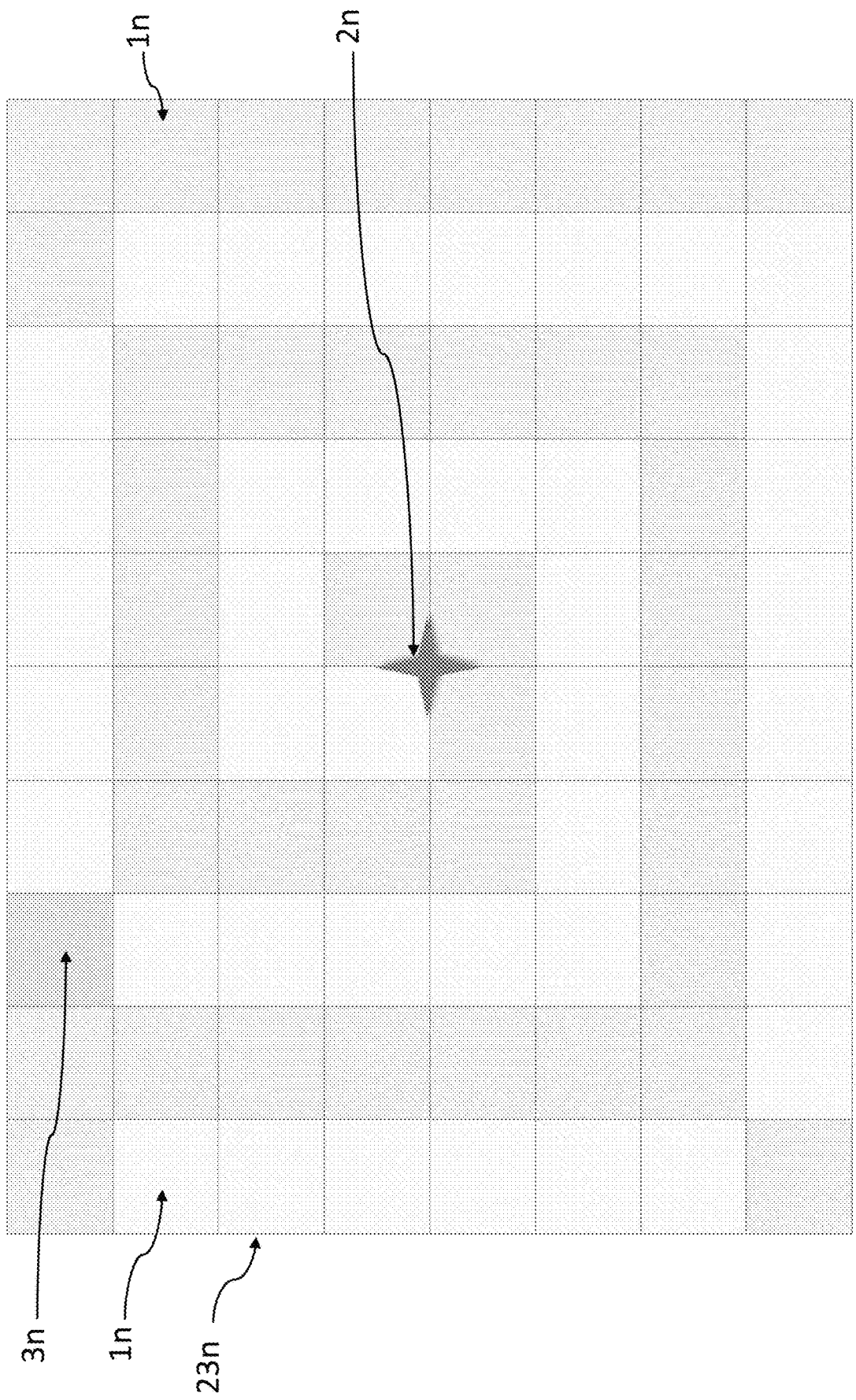
Figure 8:
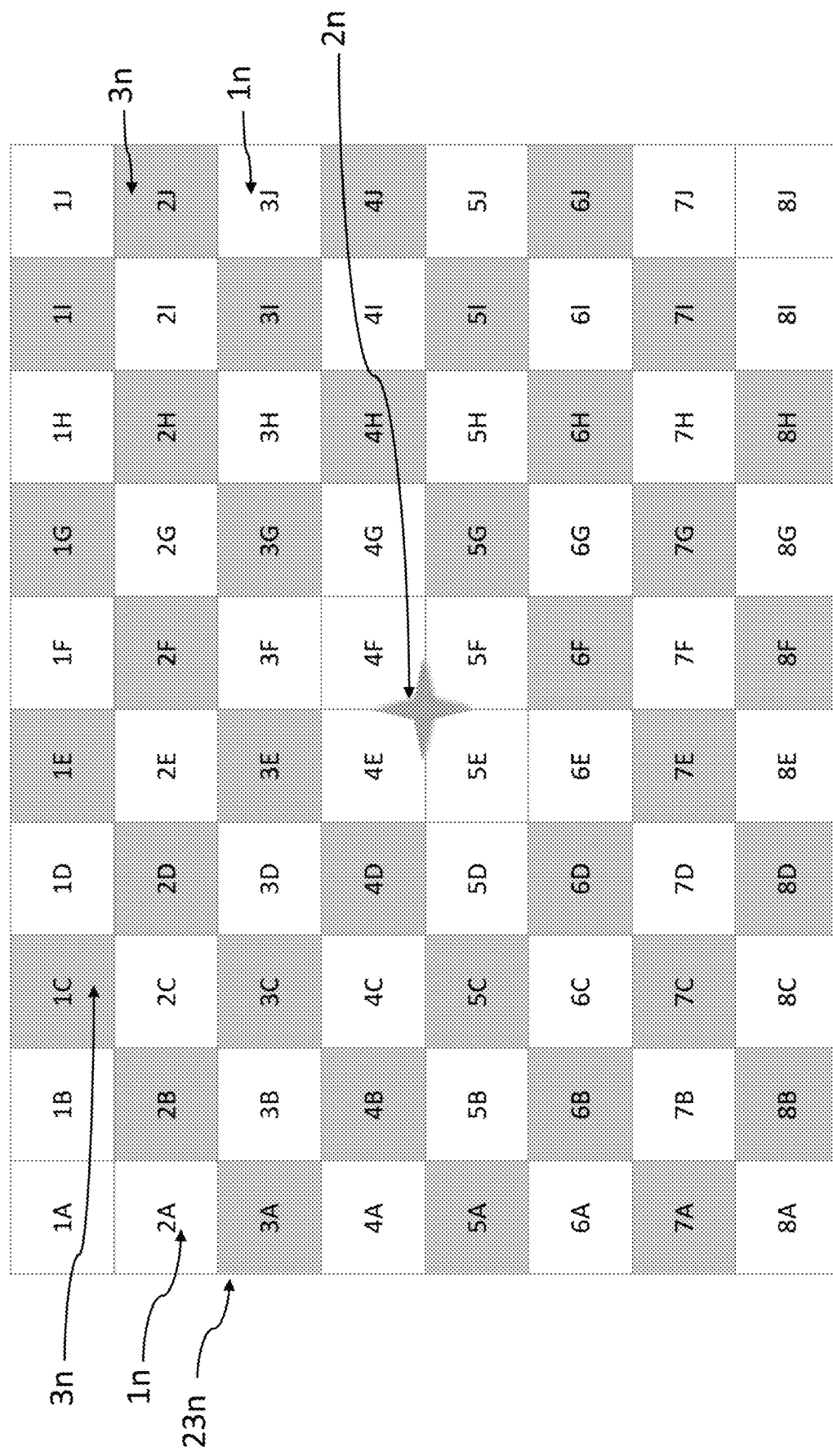
Figure 9:
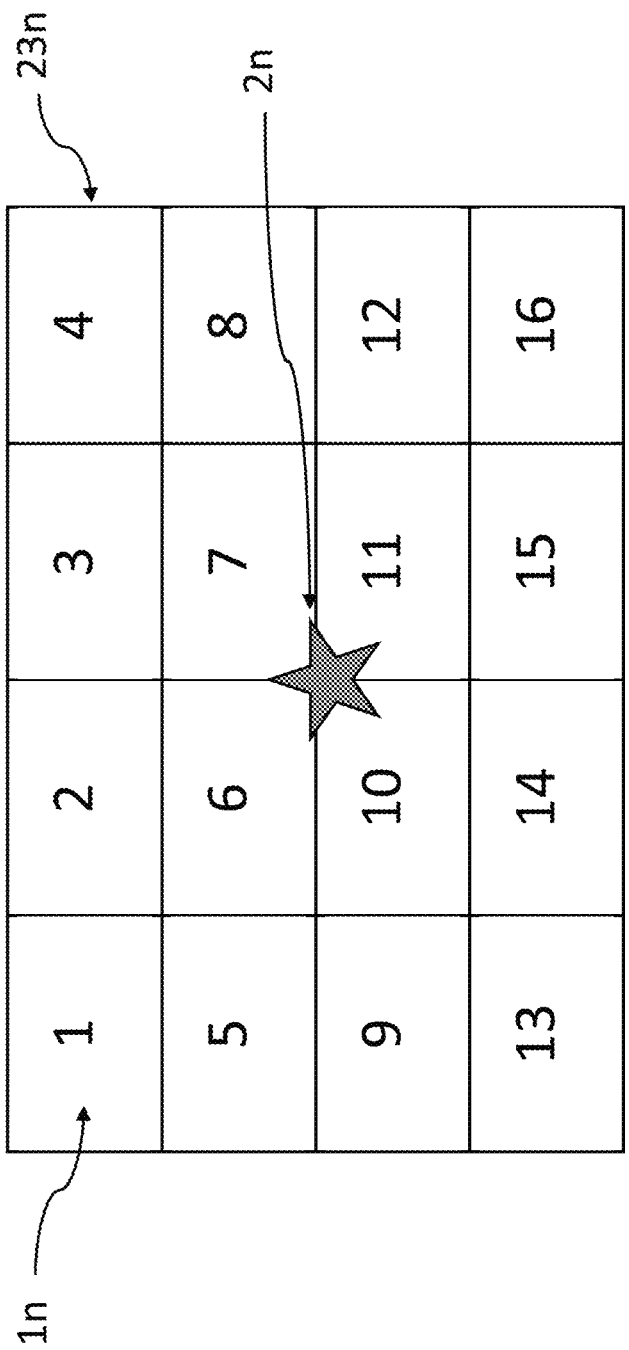
Figure 10:
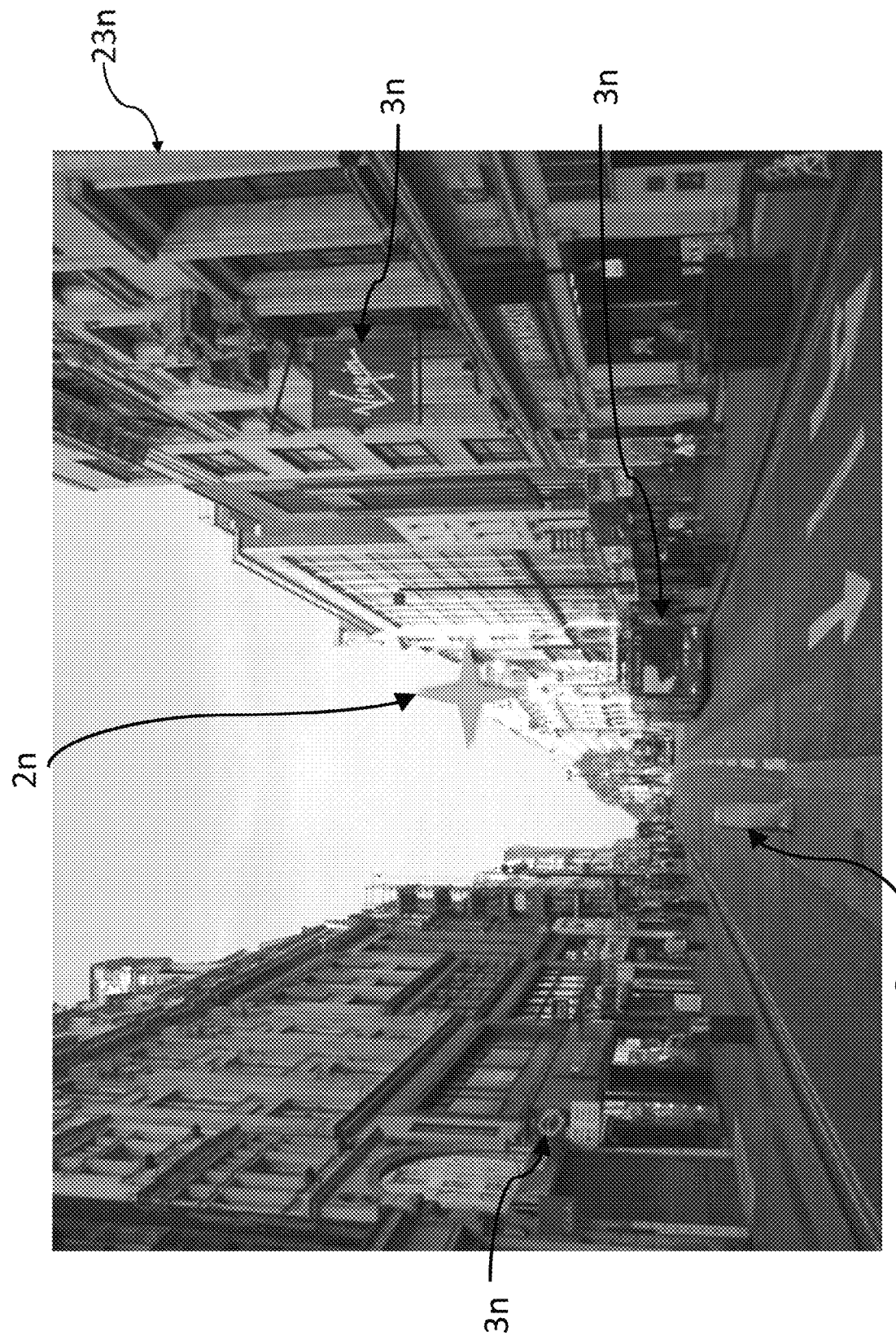

3 and/or the preferred alternative system for calibrating a display for a visual field test of FIG. 4, as well as the preferred method for calibrating a display for a visual field test shown in FIG. 2;

FIG. 6 shows a preferred test image of a geometric pattern including a preferred visual field test graphic made in accordance with a preferred embodiment of the present invention and being suitable for use with the preferred method and/or system for testing for visual function as shown in FIG. 1, and where the focus point is not in the centre of the preferred test image;

FIG. 7 shows a further preferred test image of a geometric pattern comprising different visual tones defined by the loci of an 8 by 10 grid, and includes a preferred target locus of a different tone to the remaining non-target loci, and also includes a preferred focus point positioned within the grid, the preferred test image also being suitable for use with the preferred method and/or system for testing for visual function shown in FIG. 1;

FIG. 8 shows yet a further preferred test image of an alternative geometric pattern to that of FIG. 7 comprising two visual tones defined by the loci of an 8 by 10 grid, and also includes a preferred focus point positioned within the grid, the preferred test image also being suitable for use with the preferred method and/or system for testing for visual function shown in FIG. 1;

FIG. 9 shows still yet a further preferred test image which may be divided into 16 loci by way of a 4 by 4 grid, and which may include a preferred focus point positioned within the grid, the preferred test image also being suitable for use with the preferred method and/or system for testing for visual function shown in FIG. 1; and, FIG. 10 shows still yet a further preferred test image, which may be used as part of a test question, as it may appear to a user during a visual function test, the preferred test image also being suitable for use with the preferred method and/or system for testing for visual function shown in FIG. 1.

MODES FOR CARRYING OUT THE INVENTION

In the following detailed description of the invention, reference is made to the drawings in which like reference numerals refer to like elements throughout, and which are intended to show by way of illustration specific embodiments in which the invention may be practiced. It is to be understood that other embodiments may be utilised and that procedural and/or structural changes may be made without departing from the spirit and scope of the invention.

Unless specifically stated otherwise as apparent from the following discussion, it is to be appreciated that throughout the description, discussions utilising terms such as "processing", "computing", "calculating", "acquiring", "transmitting", "aggregating", "receiving", "retrieving", "identifying", "determining", "analysing", "manipulating" and/or "displaying", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Discussions and direct or indirect reference regarding any apparatus for performing the operations of the invention are provided herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), erasable programmable read-only memory (EPROMs), electrically erasable programmable read-only memory (EEPROMs), magnetic or optical cards, or any type of media suitable for storing electronic instructions, and each coupled to a computer system bus.

The software modules, applications, or any engines and displays or any GUIs presented or discussed directly or indirectly herein are not inherently related to any particular computer or other apparatus. Various general-purpose systems may be used with programs in accordance with the teachings herein, or it may prove convenient to construct more specialised apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

Although separate modules, applications or any engines (e.g. module(s)/application(s) and database(s)/storage device(s) are described including with reference to one or more network server, each for effecting specific preferred aspects (or combinations thereof) of the method and/or system, it should be appreciated that any number of modules/applications/engines/databases/storage devices for performing any one, or any suitable combination of, aspects of method and/or system, could be provided (wherever required) in accordance with the present invention. A person skilled in the relevant art will appreciate many such module(s)/application(s)/engine(s) and databases(s)/storage devices, embodiments, modifications, variations and alternatives therefor, and as such the present invention should not be construed as limited to any of the examples provided herein and/or described with reference to the drawings.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

In FIG. 1 of the drawings there is shown a block diagram of a preferred method and/or system 10 (hereinafter generally referred to as "method 10" for simplicity) for enabling a user 11$n$ to perform a preferred visual function/field test (hereinafter "visual function test" or "visual field test") by way of a user operable device 12$n$. Method 10 is suitable for use over a communications network(s) 80$n$, such as, for example, the Internet, as shown. It should be understood however, that method 10 of the present invention is not limited to that use only.

The term "user operable device 12$n$" refers to any suitable type of computing device or software application, etc., capable of transmitting, receiving, capturing, conveying and/or displaying data as described herein, including, but not limited to, a mobile or cellular phone, a smart phone, an App, a smart watch or other wearable electronic device, an augmented reality device, a connected Internet of Things ("IoT") device; a Personal Digital Assistant (PDA), and/or any other suitable computing device, including a server, personal, desktop, tablet, notebook computer or any combination thereof or combination of sub-components thereof.

To start the preferred visual function test (hereinafter simply referred to as "test"), method 10 commences at block 14, whereat a user 11n may request the performance of the test via a user operable device 12n. At block 15 a display 13n (see, for example, FIGS. 3 and 4) associated with the user operable device 12n can be calibrated according to the preferred method for calibrating a display 15A of FIG. 2, using preferred system 15B of FIG. 3, or the alternative preferred system of 15C of FIG. 4, or any other suitable system (not shown). The steps of method 15A for calibrating a display in FIG. 2 can be performed on a suitable combination of the display 13n of a user operable device 12n such as in FIG. 3 or 4, and preferably includes measuring test-local light conditions 15(i), including those light conditions 13A local to the display, to acquire test-local light conditions data 15(ii), processing the acquired test-local light conditions data 15(iii) to determine display calibration values 15(iv) and then calibrating the display 13n using one or more pre-determined values and/or the values determined during the display values determination step 15(v) of the method for calibrating a display 15A, thus allowing for the display 13n to be preferably appropriately calibrated for the test according to method 10. Calibrating the display 13n provides more consistent results as between separate tests and within individual tests to promote overall test accuracy.

Figure 3:
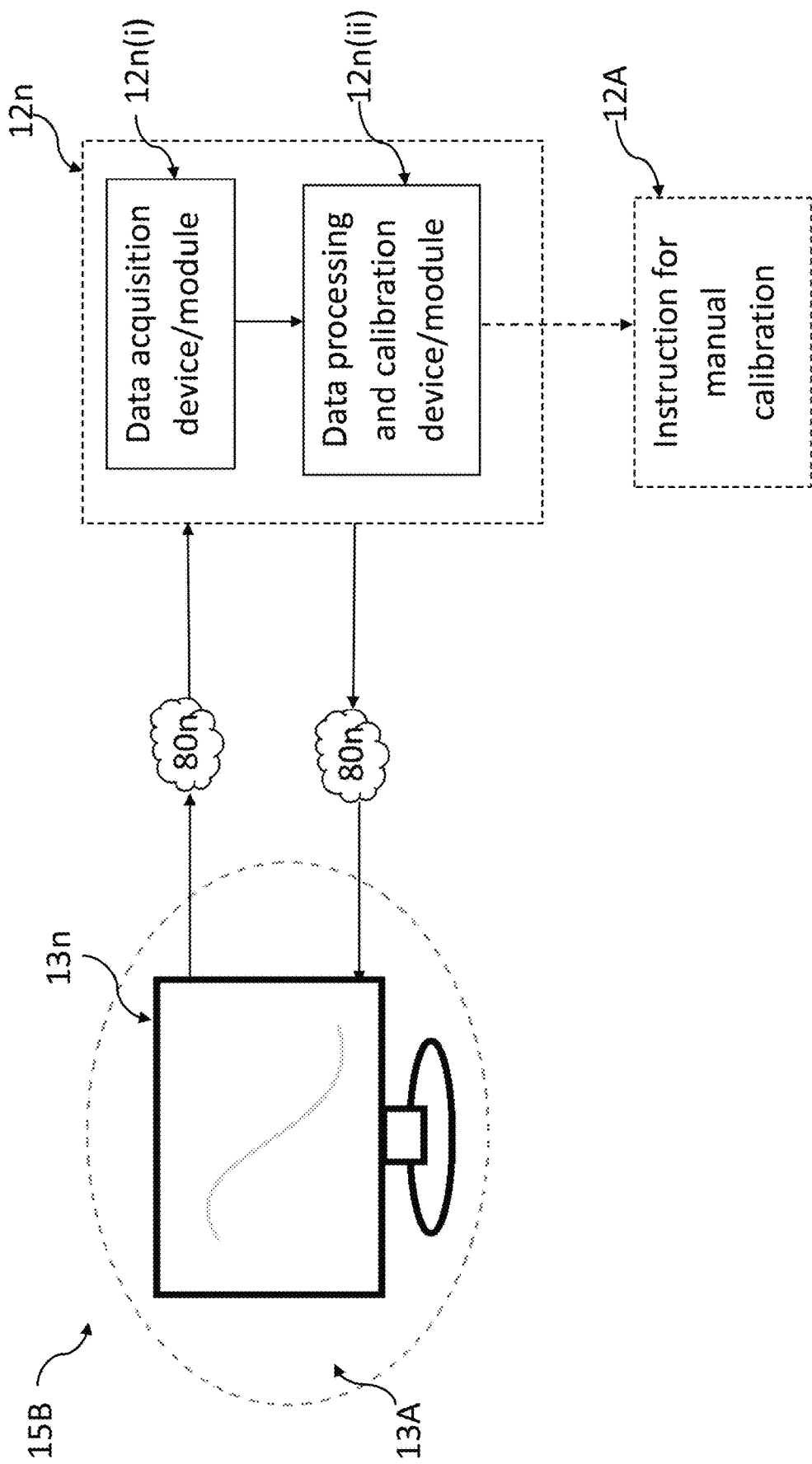
FIG. 3 is a block diagram which illustrates a preferred system for calibrating a display for a visual field test including a display associated with a user operable device, made in accordance with a preferred embodiment of the present invention and being suitable for use with the preferred method and/or system for testing for visual function shown in FIG. 1 and/or the method for calibrating a display for a visual field test shown in FIG. 2.

Preferred system 15B of FIG. 3 includes a display 13n for displaying the visual function test, display 13n being preferably in communication with a user operable device 12n via a communication network 80n, such as a cellular network (not shown). System 15B preferably utilises a data acquisition device/module 12n(i) for acquiring test-local light conditions 13A data, and a data processing device/module 12n(ii) to process the acquired test-local light conditions 13A data and to determine the calibration values, and also to calibrate the display 13n. In an alternative preferred system 15C, shown in FIG. 4, a test target 3n displayed on display 13n forms part of the test-local light conditions 13A, and mobile device 12n (user operable device 12n) is used to measure 15(i) and acquire test-local light conditions data 15(ii), process the test-local light conditions data 15(iii), determine display calibration values 15(iv), and calibrate the display 15(v). In either preferred system 15B or 15C, the display 13n may be calibrated manually on the display 13n following instructions 12A for manual calibration obtained from the data processing and calibration device/module 12n(ii) or mobile device 12n of the respective systems 15A or 15B. In an embodiment, the instructions for manual calibration 12A may be presented on display 13n and so that user 11n can calibrate by toggling appropriate display controls (not shown) themselves.

User 11n is then preferably prompted or otherwise, at block 16, to provide predetermined user 11n details (hereinafter simply referred to as "user data"). Preferred user data may include, but is not limited to, the user's 11n name, gender, age, contact telephone number, location, etc. The user data provided at block 16, of method 10, is then captured and stored on a data storage device(s) or module(s) 17n which is preferably part of a data and analysis module(s) 50, which is hosted or otherwise provided by one or more network server(s) (not shown). The preferred process of capturing and storing user data on data storage device(s) or module(s) 17n, is represented by block 51 within preferred data and storage module(s) 50.

At block 18 the user 11n is prompted to perform a blind spot determination test. The blind spot determination test, or a suitable adaptation thereof, is used to determine the location of the user's 11n blind spot—this information can be used to determine if the user 11n is suitably distanced from the display 13n, and also used to more precisely map the test loci on the display 13n. Once the blind spot is determined it can be employed during the visual field test according to method 10 to determine user fixation loss from focus point 2n by presenting a graphic (not shown) at the location of an initially determined blind spot (not shown) so that if user 11n looks away from focus point 2n the graphic becomes visible to the user 11n and the user 11n is thereby alerted that they have lost fixation on focus point 2n. In the event that user 11n has lost fixation due to, for example, moving away from or closer to the display 13n during the test, the blind spot test can be performed again to determine the user's 11n new location in reference to the display 13n and used to calibrate the loci 1n parameters, including the number of loci 1n as well as loci 1n geometry, or any other parameters, to suit the new location of the user 11n in reference to display 13n.

An instruction page(s) or GUI(s) (not shown), which can include an animation, video or voice recording to provide instructions on how to take the test is then preferably presented to user 11n, at block 19, which preferably includes instructing user 11n to conduct the test monocularly, wherein user 11n is instructed to keep one eye covered at a time during the whole or part of the test. At this point of preferred method 10, i.e. at block 19, user 11n may also be instructed to take the test undisturbed, in a sufficiently darkened room, and informed of the duration of the test which may take approximately 15 to 20 minutes, or any other suitable time as required or desired. Method 10 then continues at block 20, whereat a general question screen(s) or GUI(s) (not shown) is preferably displayed to the user 11n, which can provide further instruction or additional information, including providing a list of test questions, and which also allows user 11n to initiate the presentation of the test questions, at block 22, in order to continue the preferred test of method 10.

After initiating the presentation of the test questions, at block 22, a series of test questions in the form of timed tasks are presented to user 11n iteratively. In a preferred embodiment of method 10 of the present invention, one or more test image(s) 23n of geometric pattern(s) comprising at least two different visual tones defined by sectors 1n (hereinafter referred to as "loci 1n"), arranged within a preferred 8 by 10 grid (examples of which are shown in, for example, FIGS. 7 and 8) may be presented to user 11n with at least one test target 3n (as best shown in, for example, FIG. 7) disposed therein. The one or more test target(s) 3n may be one or more loci 1n (i.e. test loci 3n) and may have a tonal value different to other non-target loci 1n. The tonal value of the one or more test loci 3n may correlate to a test difficulty level of one of a number of difficulty levels, such as, for example, four preferred levels of difficulty. In further preferred embodiments, any visual value of any loci 1n, test target 3n, or test image 23n may be assigned a correlated test difficulty level.

In one embodiment of preferred method 10, the test may involve presenting still or animated images 23n (as will be described in further detail below with reference to, for example, FIGS. 7 to 10) of common objects, virtual scenes of daily life, or other suitable images, that are preferably formed composite with the aforementioned grid-based patterns (not shown), along with respective test targets 3n (examples of which are shown in FIG. 7 to 10) to be identified and selected by user 11n. The common objects or virtual scenes preferably include, but are not limited to, objects and scenes such as: a street scene (such as, for example, that depicted in FIG. 10; faces in a crowd; hidden objects; camouflaged animals; a cutlery drawer; persons or objects in a crowded room; shadowy furniture; a newspaper; and/or, any other test image 23n determined to be suitable. Test targets 3n to be identified and selected within test images 23n preferably include, but are not limited to: symbol(s)/letter(s); an object(s) or part(s) of an object(s); a graphic; a moving, animated, vibrating or spinning object(s); and/or, any other test target 3n determined to be suitable. For example, referring to FIG. 10, test targets 3n could be a bollard 3n, a shop sign 3n, flag 3n, or a bus 3n. One practical preferred embodiment of preferred method 10, may also involve hazard perception driving videos, traffic light changes, locating vehicles and associated objects on a road, and similar. It will be appreciated that the type of test image(s) 23n used, and the test target(s) 3n to be identified therein, is/are not limited, and new test images 23n and test targets 3n may be deemed suitable by, for example, testing their ability to generate accurate test results.

More specifically, a given timed task (of a test question, presented to user 11n, at block 22) may require user 11n attempting to correctly select or identify a test target 3n located in one of any suitable number of loci 1n, e.g. in one of 52 of 80 numbered loci 1n as shown, for example, FIG. 7 or 8, defined by preferred gridlines, which can be visible or invisible to the user 11n, as is illustrated by way of the exemplary test images 23n shown in FIGS. 7 to 9. The test may be grouped for scoring based on which loci 1n is being tested. Each locus 1n may be tested by a number of test questions of varying levels of difficulty and duration, resulting in a number of response data values being generated per locus 1n. The relative difficulty of each timed task may be predetermined by any suitable predefined test, data or analysis, such as, for example, a suitable Item Response Theory ("IRT") analysis, such as, for example, a Rasch analysis or Partial Credit model analysis, performed on sample evaluation among a cohort of healthy controls and glaucoma patients of different severity levels by an IRT analysis module 53n (see, FIG. 1).

Test questions, presented at block 22, of preferred method 10, may involve specific peripheral vision testing in which a predefined focal point 2n, such as, for example, a still or spinning star 2n, may be presented as an initial focus starting point during the test, as shown in, for example, FIGS. 6 to 10. The focal point (hereinafter simply referred to as "star 2n"), may be located anywhere on the test image 23n, including at a suitable intersection of gridlines, such as, for example, at the centre of the image 23n as shown in, for example, FIGS. 7 to 10, or at another suitable location as shown in FIG. 6. Users' 11n may be asked to make selections while focusing their vision on star 2n, or may be asked to focus on star 2n initially, and then subsequently be permitted to move their eyes and/or head to complete a given timed task.

A test target 3n within a test image 23n, presented as part of a test question, at block 22, of preferred method 10, may be selected or otherwise identified, or in a preferred form of the test only the presence or absence of a test target 3n identified, by the user 11n, for example: utilising a mouse, or other GUI pointing device (not shown), to click or otherwise select a potential test target 3n; touching a touchscreen; or answering or otherwise replying to a task question either verbally or by way of a gesture, etc. A given test question may have multiple test targets 3n per image 23n. Test targets 3n are preferably vetted for repeated test takers (i.e. users 11n) to avoid repetition so that users 11n do not habitually learn the correct test target 3n locations and generate erroneous results.

Test targets 3n, and test images 23n, can be sourced from a pool of prior test images 23n stored on the network server(s) (not shown) which hosts or otherwise maintains/provides data and analysis module(s) 50, or they may be obtained from other suitable data source(s) 60n, including, for example, external data source(s) 60n readily accessible over the internet (communications network(s) 80n). Test target 3n and/or test image 23n opacity, dimensions and other characteristics may be predetermined, altered and/or adjusted as required or desired.

A suitable test question (and its test image 23n, with test targets 3n contained therein) may appear to user 11n, at block 22, of preferred method 10, in the format as shown in any one of FIGS. 6 to 10.

The completion of the test questions (presented at block 22) is rated on Pass 26 (block 26) or Fail 24 (block 24) gradings, as shown in FIG. 1. The gradings are preferably measured by two parameters: the correct completion of the timed task, and, completion of the timed task in the allocated time. A Pass (at block 26) is achieved when both parameters are satisfied, that is, when user 11n finds the requested test target 3n object(s) in allocated time, and user 11n Fails (at block 24) a test question when they are unable to correctly identify the test target 3n object(s) in the allocated time.

The test of preferred method 10, continues for a predetermined number of iterations (as indicated by block 30), until all the test questions are completed by user 11n and a result can be generated to be selectively provided to user 11n. Following each test question, the response value (i.e. Pass or Fail, at blocks 26 or 24) and the time taken to select a target (i.e. the response time), both of which can be referred to as response data, is/are sent/captured by data and analysis module(s) 50, as is indicated by block 28.

Following the capture/acquisition of user 11n response data at block 28, all obtained response data is consolidated/aggregated, at block 52, with the preferred user data that was captured/acquired/stored at block 51, and thereafter, the consolidated/aggregated data is analysed against a population database (stored on the network server(s) (not shown) associated with data and analysis module(s) 50) that has been validated and vetted/calibrated against a cohort of glaucoma patients of various levels of visual function, and/or any other suitable cohort, and/or any data acquired from any prior visual field tests. This step/stage being preferably accomplished by a test algorithm module(s) 53n, and optionally an IRT analysis module(s) 53n, an eye locus performance map module(s) 53n, and/or an artificial intelligence module(s) 53n (which may be separate or consolidated module(s) 53n) associated with, or of, data and analysis module(s) 50. This analysis and specifically the test algorithm of the module(s) 53n may be based on a suitable algorithm or test as required or desired.

The test algorithm(s) of module(s) 53n assess a user's 11n visual function relating to glaucoma for each of the loci 1n of the test image 23n, such as, for example, the loci 1n of the test images 23n shown in FIGS. 7 to 9. A staircase method is preferably used in the test algorithm of module(s) 53n, where the difficulty level of subsequent test questions is based on the time taken to select a target and/or success of previous test questions and optionally compared to predetermined control values, such as, for example, an age-matched cohort sample. When sufficient response data per tested loci is acquired (at blocks 28 & 52), that response data can be used to generate a map per eye locus, as is indicated by way of block 54. Preferably, two global summary scores for each eye may also be produced: a mean ability and a variation between loci scores. The map per eye locus and global summary scores, generated at block 54, may then be provided to user 11n, and/or may be stored (e.g. in data storage device(s) or module(s) 17n, or externally in, for example, an associated cloud (not shown)) for future access/retrieval purposes.

The reliability of the test of preferred method 10, of the present invention, may be monitored by the test algorithm module(s) 53n, including the or its artificial intelligence module 53n, and/or any another suitable module(s) 53n, such that, for example: false positives may be recorded by the number of incorrect answers; false negatives may be tested by evaluating question tests of lower difficulty than a predetermined difficulty for one or more particular loci 1n, etc. Fixation loss/reversion to binocularity may also be preferably tested by evaluating test question response times/items in test questions which are of higher difficulty than a predetermined difficultly level for one or more particular loci 1n, e.g. in the one or more loci 1n of the exemplary test images 23n shown in FIGS. 7 to 9.

Figure 5:
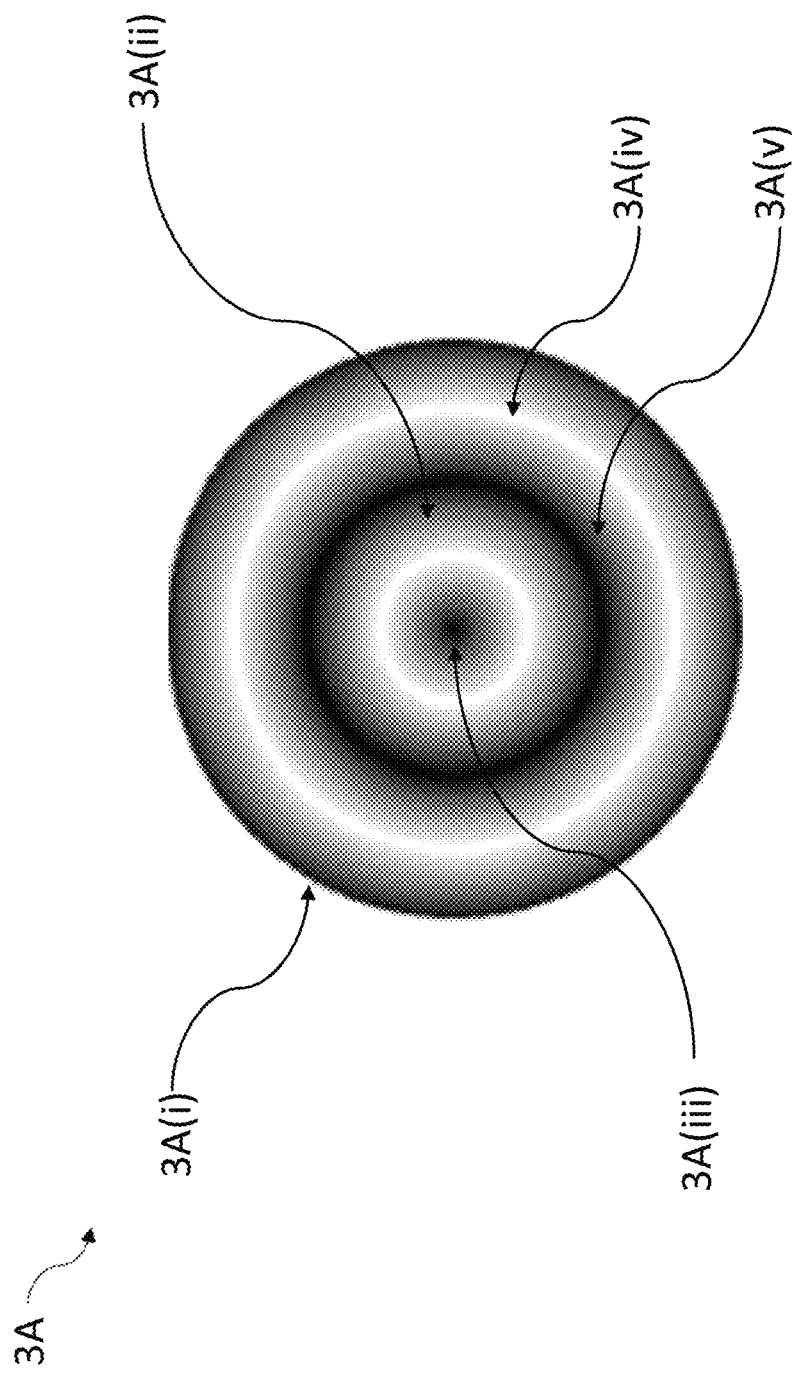
FIG. 5 shows a preferred circular visual field test graphic with a sinusoidal waveform traversing the centre and perimeter of the visual field test graphic made in accordance with a preferred embodiment of the present invention and being suitable for use with the preferred method and/or system for testing for visual function shown in FIG. 1, and the preferred system for calibrating a display for a visual field test of FIG.

According to preferred method 10 the test target 3n may include or may preferably be in the form of a test graphic 3A as shown in FIG. 5, where the graphic preferably has a circular perimeter 3A(i) and includes a sinusoidal waveform 3A(ii) traversing the center 3A(iii) and the circular perimeter 3A(i). The peaks 3A(iv) and troughs 3A(v) of the sinusoidal waveform 3A(ii) preferably define luminance-configured graphic segments where the luminance is a relative luminance RL which has preferably been determined by the following mathematical steps:

assigning each Red/Green/Blue ("RGB") colour component an integer value ("$C_{RGB}$") between 0 and 255;
converting each component's $C_{RGB}$ integer value to equate with a respective component decimal value ("$C_D$"), which is calculated as $C_{RGB}/255$;
if the $C_D$ of a component >0.03928, applying the formula $CL=(C_D+0.055/1.055)^{24}$ to determine the linear value of the component ("CL"); if the $C_D$ of a component <0.03928, applying the formula $C_L=(C_D/12.92)$ to determine the linear value of the component ("$C_L$");
adding the $C_L$ of each component to obtain a relative luminance ("RL").

In preferred method 10 one or more luminance of the one or more luminance-configured colours of one or more graphic segments defining one or more sinusoid peaks 3A(iv) and/or troughs 3A(v) may be configured with a relative decibel valued (rdB) colour using the following formula: $rdB=-2\log(RL1-RL2)/(RL1+RL2)$, to obtain rdB resembling standard automated perimetry range, being 30 to 46 dB. One or more luminance-configured colours defining one or more sinusoid peaks 3A(iv) and/or troughs 3A(v) wherein the luminance has been configured with an RL or rdB value, can be assigned to one or more difficulty levels of the visual field test according to method 10.

A luminance-configurable colour in preferable embodiment of visual field test graphic 3A (best shown in FIG. 5), can be displayed by cyclically fading (or transitioning) the luminance-configurable colour in or out (or both) in a given graphic segment defining a sinusoid peak 3A(iv) or trough 3A(v), and/or fading to and/or from (or both) another luminance-configurable colour defining a peak 3A(iv) or trough 3A(v). A display cycle from one luminance-configurable colour to another and back can be made at a frequency selected from preferred frequency range of approximately 10 Hz to 110 Hz, for a preferable display period of about 0.55 seconds.

In the preferred embodiment of visual field test graphic 3A the display cycle may involve a peak 3A(iv) having a first luminance-configurable colour transitioning (or fading) to a trough 3A(v) and back to the peak 3A(iv) in the same graphic segment, there being two or more graphic segments and in each adjacent graphic segment the opposite of a peak 3A(vi) or trough 3A(v) being displayed, thus forming sinusoidal waveform 3A(ii) where each peak 3A(iv) transitions to a trough 3A(v) and back in an undulating display cycle. It should be appreciated that a display cycle may start at any point between the transition from/to a peak 3A(iv) or a trough 3A(v).

During each display period, the luminance-configurable colours may be displayed to vary in contrast and preferably so that initial display cycles have less contrast and increase to having higher contrast in latter display cycles. In an alternative preferred method 10 contrast may increase across a number of periods.

It will be appreciated that the shape of the visual field test graphic 3A does not need to be circular, and sinusoidal waveform 3A(ii) may traverse the graphic 3A other than by from the perimeter 3A(i) to the center 3A(iii). To remove any doubt, reference to a peak also refers to the whole of a positive part of a waveform cycle, and reference to a trough also refers to the whole of a negative part of a cycle.

Referring to FIG. 6, the test target 3n includes the visual field test graphic 3A as presented within a test image 23n of an array of forms, the tonality of visual field test graphic 3A having being adjusted to show a lighter tonal value.

Artificial intelligence in the form of one or more artificial intelligence algorithm(s), module(s) or application(s) (hereinafter collectively referred to as artificial intelligence module(s) 53n) which use machine or deep learning (as shown in FIG. 1) in association, or combination with, various other software and/or hardware module(s) or application(s) (e.g. module(s) 53n) is preferably adapted to analyse any/all acquired/consolidated/aggregated user data, response data, result data and map of eye performance data collected and/or otherwise acquired/aggregated, etc., by data and analysis module(s) 50, and/or data sources 60n, either periodically or live (or substantially in real-time), and/or during the test, of preferred method 10, being conducted, and/or after each or any step of preferred method 10, and is also preferably adapted to optimise the performance of the test and improve test accuracy. Artificial intelligence module(s) 53n may also preferably be used to monitor change over time of the test(s) to determine if an individual's 11n vision and/or level of glaucoma has worsened over time. This change over time may be represented and/or conveyed to the user 11n by any suitable means, but is preferably conveyed graphically by any suitable means by way of method 10. Thus, a user 11n may repeat the test over a period of time and be able to see whether their vision has worsened since their first of subsequent test(s) in accordance with method 10.

The artificial intelligence module(s) 53n is also adapted to directly interact with the data module(s) 53n, test algorithm module(s) 53n, IRT algorithm module(s) 53n, and map of eye locus performance module(s) 54 and/or one or more aspects of any one or more of the mentioned module(s) 53n, other suitable modules which may be added as part of the method 10, as well as the instructions from the non-transitory computer readable medium of the present invention, and/or of any suitable system that may be deployed in accordance with the present invention.

Artificial intelligence module(s) 53n is also preferably specifically adapted to predetermine and/or generate any content and parameters of the test, including, but not limited to: the test images 23n; test targets 3n (within test images 23n); test graphic(s) 3A; test duration; loci 1n, gridline numbers, etc.; test target 3n opacity; difficulty of the test; focal point 2n; and focal point 2n location, based on any data available to artificial intelligence module(s) 53n resulting from any part or stage of preferred method 10, etc., any instructions of/for a non-transitory computer readable medium, and/or any part of any preferred practical system of the present invention.

Artificial intelligence module(s) 53n is also preferably adapted to select suitable test images 23n and test targets 3n including test graphic(s) 3A (within test images 23n), as required or desired, based on comparing/vetting their suitability against, for example, previously selected test images 23n and test targets 3n, test graphic(s) 3A, etc.

Preferred method 10 of the present invention, may be performed wholly or partially using one or more computing devices (i.e. network server(s)—not shown) executing a set of instructions of the method 10, which may be sourced and then executed from a non-transitory computer readable medium (not shown) associated with the one or more computing device(s) (i.e. network server(s)—not shown) which store or otherwise contains/provides the instructions.

Preferred method 10 of the present invention may be performed wholly or partially by a system (e.g. shown in FIG. 1) which includes one or more visual field test module(s) or application(s) 50; one or more algorithm module(s) or application(s) 53n; one or more data module(s) 17n/52n/53n; one or more IRT analysis algorithm module(s) 53n; one or more eye locus performance map module(s) or application(s) 53n/54; and one or more artificial intelligence and/or machine learning and/or deep learning module(s) or application(s) 53n, and/or any other module(s)/application(s) deemed suitable.

It will be appreciated the method 10 may be performed by a system that includes distributing one or more aforementioned module(s)/application(s) 50/53n across such a system, including one or more network server(s) and/or computing device(s) and/or computing mean(s) (not shown), and one or more user operable devices 12n, that are all preferably operable over communications network(s) 80n.

It will be appreciated that the one or more network server(s) (not shown) associated with data and analysis module(s) 50 is/are preferably configured to communicate with user operable devices 12n, and data source(s) 60n, via any suitable communications connection(s) or network(s) 80n. Data source(s) 60n may be configured to transmit and receive data to/from network server(s) (now shown) associated with data and analysis module(s) 50, via one or more communications network(s) 80n. User operable devices 12n may be configured to transmit, receive capture and/or display data, including test question data from/to the network server(s) (not shown) associated with data and analysis module(s) 50 via one or more communications network(s) 80n. Each user operable device 12n and data source(s) 60n provider, may communicate with the network server(s) (not shown) associated with data and analysis module(s) 50 via the same or a different communications network(s) 80n. Suitable communications network(s) 80n include, but are not limited to: a Local Area Network (LAN); a Personal Area Network (PAN), as for example an Intranet; a Wide Area Network (WAN), as for example the Internet; a Virtual Private Network (VPN); a Wireless Application Protocol (WAP) network, or any other suitable telecommunication network, such as, for example, a GSM, 3G, 4G, 5G, etc., network; Bluetooth network; and/or any suitable WiFi network (wireless network). The network server(s) (now shown) associated with data and analysis module(s) 50, data source(s) 60n providers, and/or user operable device(s) 12n, may include various types of hardware and/or software necessary for communicating with one another via the one or more network(s) 80n, and/or additional computers, hardware, software, such as, for example, routers, switches, access points and/or cellular towers, etc. (not shown), each of which would be deemed appropriate by persons skilled in the relevant art.

For security purposes, various levels or security, including hardware and/or software, such as, for example, application programming interfaces (or "APIs"), firewalls, tokens, two-step authentication (not shown), etc., may be used to prevent the unauthorized access to, for example, the network server(s) (now shown) associated with data and analysis module(s) 50, and/or data source(s) 60n. Similarly, the network server(s) (not shown) associated with data and analysis module(s) 50 may utilise security (e.g. hardware and/or software—not shown) to validate access by user operable devices 12n. It is also preferred that the network server(s) (not shown) associated with data and analysis module(s) 50 performs validation functions to ensure the integrity of data transmitted between data source(s) 60n and/or user operable devices 12n. A person skilled in the relevant art will appreciate such technologies and the many options available to achieve a desired level of security and/or data validation, and as such a detailed discussion of same will not be provided. Accordingly, the present invention should be construed as including within its scope any suitable security and/or data validation technologies as would be deemed appropriate by a person skilled in the relevant art.

Communication and data transfer between the network server(s) (now shown) associated with data and analysis module(s) 50, data source(s) 60n and/or user operable devices 12n, may be achieved utilising any suitable communication, software architectural style, and/or data transfer protocol, such as, for example, FTP, Hypertext Transfer Protocol (HTTP), Representational State Transfer (REST); Simple Object Access Protocol (SOAP); Electronic Mail (hereinafter simply referred to as "e-mail"), Unstructured Supplementary Service Data (USSD), voice, Voice over IP (VoIP), Transfer Control Protocol/Internet Protocol (hereinafter simply referred to as "TCP/IP"), Short Message Service (hereinafter simply referred to as "SMS"), Multimedia Message Service (hereinafter simply referred to as "MMS"), any suitable Internet based message service, any combination of the preceding protocols and/or technologies, and/or any other suitable protocol or communication technology that allows delivery of data and/or communication/data transfer between network server(s) (not shown) associated with data and analysis module(s) 50, data source(s) 60n and/or user operable devices 12n, in accordance with preferred method 10 of the present invention. Similarly, any suitable data transfer or file format may be used in accordance with preferred method 10 of the present invention, including (but not limited to): text; a delimited file format, such as, for example, a CSV (Comma-Separated Values) file format; a RESTful web services format; a JavaScript Object Notation (JSON) data transfer format; a PDF (Portable Document Format) form at; and/or, an XML (Extensible Mark-Up Language) file format.

It will be appreciated that the illustrated invention provides an easy, objective method and/or system 10 for detecting glaucoma that is reflective of real-world visual function and which can be taken by an individual 11n on a user operable device 12n in an individual's 11n home or at another convenient location.

While this invention has been described in connection with specific embodiments thereof, it will be understood that it is capable of further modification. The present invention is intended to cover any variations, uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the attached claims. Various modifications and equivalent arrangements are intended to be included within the spirit and scope of the invention. Therefore, the specific embodiments are to be understood to be illustrative of the many ways in which the principles of the present invention may be practiced.

Where the terms "comprise", "comprises", "comprised" or "comprising" are used in this specification, they are to be interpreted as specifying the presence of the stated features, integers, steps or components referred to, but not to preclude the presence or addition of one or more other features, integers, steps, components to be grouped therewith.

The invention claimed is:

1. A method for performing a subjective visual field test to evaluate a user's monocular peripheral vision at specific loci, without a need for dedicated professional equipment or qualified professional supervision, but instead via use of at least one computing device configured to access at least one dedicated visual field test server accessible via a communications network, the method including:
   receiving a request from a user to perform a visual field test via the at least one computing device;
   acquiring predetermined user identification data from the user and/or the at least one computing device in response to predetermined instructions from the at least one dedicated visual field test server;
   presenting or providing for a required number of iterations at least one test image to the user via at least one display of the at least one computing device, the at least one test image including at least one test target contained therein that is shown at at least one predetermined location in the user's peripheral visual field, whilst the user is gazing at a focus point;
   instructing the user to identify if they have detected the presence of at least one of the at least one test target(s) contained within the at least one test image;
   acquiring response data associated with the user's attempt to identify the at least one test target(s) contained within the at least one test image;
   aggregating and/or analysing, via the at least one dedicated visual test server, acquired user identification data and/or response data utilizing a test algorithm which determines overall result data; and,
   presenting or providing the visual field test overall result data to the user via the at least one computing device;
   wherein the predetermined user identification data acquired from the user and/or the at least one computing device includes data which is used to configure test parameters for performance of the visual field test:
   wherein the at least one predetermined location of the at least one test target shown in the user's peripheral visual field may vary with each required iteration of the presentation or provision of the at least one test image; and,
   wherein the at least one test target(s) is circular and waveform in appearance and the apparent waveform traverses the at least one test target(s).

2. The method as claimed in claim 1, wherein the at least one test target(s) has at least two graphic segments for alternatingly displaying in at least one graphic segment at least one luminance-configurable colour at a predetermined frequency, and wherein the waveform of the at least one test target(s) is sinusoidal with one or more of peaks or troughs of the waveform defining that at least one graphic segment.

3. The method as claimed in claim 2, wherein the at least one luminance-configurable colour includes one or more background colour of the at least one graphic segment, and wherein, the at least one luminance-configurable colour is displayed by being faded in and/or out including to and/or from the at least one luminance-configurable colour.

4. The method as claimed in claim 2, wherein the at least one luminance-configurable colour is presented at a predetermined frequency for a predetermined period in one or more intervals.

5. The method as claimed in claim 4, wherein the predetermined frequency is approximately 10 Hz to 110 Hz and the predetermined period is about 0.55 seconds.

6. The method as claimed in claim 4, wherein presentation of the at least one luminance-configurable colour creates a varied contrast during the predetermined period.

7. The method as claimed in claim 1, wherein the at least one test target(s) has a circular perimeter and the waveform traverses a center and the perimeter of the at least one test target(s).

8. The method as claimed in claim 1, further including:
   measuring test-local light conditions to acquire corresponding data, processing the test-local light conditions to determine calibration values; and,
   calibrating the at least one display according to the one or more determined or predetermined values,
   wherein, the test-local light conditions are measured via a sensor associated with the at least one display.

9. The method as claimed in claim 1, wherein the at least one test image(s) is/are animated images.

10. The method as claimed in claim 1, wherein the at least one test image(s) is/are divided into up to 80 loci by gridlines that are visible or invisible to the user, wherein the loci comprise at least one test locus and at least one non-test locus, and wherein, the up to 80 loci comprise 52 test loci.

11. The method as claimed in claim 1, wherein the at least one test image(s) includes the focus point positioned within the at least one test image(s), and wherein, the focus point is a moving optical element.

12. The method as claimed in claim 1, wherein an incorrect attempt(s) to identify the at least one test target(s) generates a false positive response data value.

13. The method as claimed in claim 1, wherein aggregating and/or analyzing, via the at least one dedicated visual field test server, the acquired user identification data and/or the response data, utilises the or a further test algorithm to optimise the performance and/or accuracy of the visual field test, and wherein, the or a further test algorithm includes artificial intelligence and/or machine learning and/or deep learning to optimise the performance and/or the accuracy of the visual field test; and wherein, the artificial intelligence and/or machine learning and/or deep learning is adapted to predetermine content and/or parameters of the visual field test, including the content and/or parameters of any one or more of the following: the at least one test image(s); the at least one test target(s); at least one test graphic(s); at least one test locus; duration for receipt of response(s); gridlines that are visible or invisible to the user; opacity of the at least one test target(s); visual field test difficulty; suitability of a position of the user relative to the at least one display; the focus point; and the focus point location, based on any user identification data and/or the response data to optimise the performance and accuracy of the visual field test.

14. The method as claimed in claim 1, further including a blind spot determination test for determining user fixation loss from the focus point.

15. The method as claimed in claim 14, wherein user fixation loss is determined by presenting a graphic at a location of the blind spot so that if fixation loss occurs the graphic becomes visible to the user.

16. The method as claimed in claim 15, wherein user fixation loss is used to calibrate loci parameters including loci number and loci geometry.

17. The method as claimed in claim 14, wherein the blind spot determination test is used to determine optimum user distance from the at least one display and precise distribution of test loci on the at least one display.

* * * * *